(12) United States Patent
Sarvazyan et al.

(10) Patent No.: US 7,713,200 B1
(45) Date of Patent: May 11, 2010

(54) WIRELESS BEACON FOR TIME-REVERSAL ACOUSTICS, METHOD OF USE AND INSTRUMENT CONTAINING THEREOF

(76) Inventors: Armen P. Sarvazyan, 1753 Linvale Harbourton Rd., Lambertville, NJ (US) 08530-3302; Stanislav Emelianov, 11520 Antigua Dr., Austin, TX (US) 78759

( * ) Notice: Subject to any disclaimer, the term of this patent is extended or adjusted under 35 U.S.C. 154(b) by 1278 days.

(21) Appl. No.: 11/223,259

(22) Filed: Sep. 10, 2005

(51) Int. Cl.
*A61B 8/00* (2006.01)
(52) U.S. Cl. .................. 600/437; 600/439; 600/447
(58) Field of Classification Search ............. 600/407, 600/447, 439
See application file for complete search history.

(56) References Cited

U.S. PATENT DOCUMENTS

| | | | |
|---|---|---|---|
| 5,092,336 A | 3/1992 | Fink | |
| 5,428,999 A | 7/1995 | Fink | |
| 6,161,434 A | 12/2000 | Fink | |
| 6,490,469 B2 * | 12/2002 | Candy | 600/407 |
| 2003/0005770 A1 * | 1/2003 | Berryman | 73/602 |
| 2004/0162507 A1 | 8/2004 | Govari | |
| 2004/0162550 A1 | 8/2004 | Govari | |

FOREIGN PATENT DOCUMENTS

EP 1449564 8/2004

OTHER PUBLICATIONS

Fink, Time-Reversed Acoustics, *Scientific American*, Nov. 1999, p. 91-97.
Arndt, Rewiring the Body, *Business Week*, p. 74-82, Mar. 7, 2005, Reprint from web site edition.

* cited by examiner

*Primary Examiner*—Eric F Winakur
*Assistant Examiner*—Helene Bor
(74) *Attorney, Agent, or Firm*—Boris Leschinsky

(57) ABSTRACT

A time-reversal acoustics system includes a wireless beacon with a piezoelectric element adapted to receive an initial acoustic signal from each of a plurality of transducers combined in a single transmitter and controlled individually by an electronic unit. The initial acoustic signal is transformed by the piezoelectric element into an electromagnetic wave feedback signal and transmitted wirelessly to the receiver connected to the input of the electronic unit. The electronic unit receives the feedback signal and transforms it using the time-reversal principles to generate a driving signal for each transducer. All such driving signals are then sent simultaneously to all transducers to deliver high intensity acoustic energy to the beacon. The invention can be used advantageously to noninvasively recharge implant batteries, control drug eluting from an implant, in an image-guided drug-delivery apparatus, etc.

10 Claims, 9 Drawing Sheets

WIRELESS BEACON FOR TIME-REVERSAL ACOUSTICS, METHOD OF USE AND INSTRUMENT CONTAINING THEREOF

This invention was made with government support under Grant 1 R21 EB001548-01 awarded by the National Institutes of Health, National Institute of Biomedical Imaging and BioEngineering. The government has certain rights in this invention.

BACKGROUND OF THE INVENTION

The present invention relates generally to beacons in the Time-Reversal Acoustics (TRA) systems used to focus acoustic waves for various useful applications in the biomedical area. More particularly, the beacon of the invention provides an electromagnetic wave signal in response to received acoustic waves, which may be used as a feedback signal for tuning time-reversal acoustic system to focus acoustic waves at the location of such beacon for various useful purposes, such as charging a battery of an implant attached to the beacon. The device and method of the invention may be used advantageously as part of a medical instrument inside a patient's body as well as for other applications described below in more detail.

For the purposes of this description, the term "patient" is used to describe any person, animal, or other living being in which the medical instrument is inserted temporarily or implanted on a permanent basis. The term "medical instrument" or just "instrument" is used to describe various medical inserts and implants such as but not limited to catheters, needles, various scopes of flexible or rigid nature, implants, stents including drug-eluting stents, pacemakers and parts thereof, implantable electrical stimulators of all kinds including neurostimulators, neuromodulation devices, vagus nerve stimulators, hypoglossal nerve stimulators, thalamus stimulators, sacral nerve stimulators and spinal cord stimulators, implantable hearing aid devices including inner ear microtransmitters, cannulas, balloons, probes, guidewires, trocars, sensors, markers, infusion pumps, various implants functioning from an internal battery, and local medication delivery devices.

In medicine, the present invention may be used most advantageously with TRA methods and devices designed for various diagnostic and therapeutic ultrasound and other acoustic wave applications including ultrasonic hyperthermia and ablation of tumors, cavitational destruction of tissues, ultrasound imaging and image-guided interventions, ultrasonic lithotripsy, ultrasound-assisted drug delivery, ultrasonic surgery, and remote charging of batteries in the implanted devices. In therapeutic applications, absorbed ultrasound energy is used to change the state of a target area. In particular, ultrasound energy applied at high power densities can induce significant physiological effects on tissues. These effects may result from either thermal or mechanical response of the tissue subjected to ultrasound energy. Thermal effects include hyperthermia and ablation of tissue. The absorption of ultrasound energy at the target area induces a temperature rise, which causes coagulation or ablation of target area cells. In therapeutic applications of ultrasound, it is important that the applied ultrasound energy causes an intended change of state solely at a target area without adversely affecting other tissue within the patient. The effective therapeutic dose must be delivered to the target area while the thermal and mechanical effects in intermediary and surrounding tissue are minimized. Therefore, proper focusing and control is one of the primary criteria for successful therapeutic application of ultrasound.

Examples of the use of ultrasound in medicine can be found throughout the prior art. U.S. Pat. No. 5,590,657 to Cain et al. describes a high intensity ultrasound system including a phased array of ultrasound transducers located outside the patient. Methods for refocusing the beam are described. U.S. Pat. No. 6,128,958 to Cain describes architecture for driving an ultrasound phased array. U.S. Pat. No. 5,769,790 to Watkins et al. describes a system for combining ultrasound therapy and imaging. U.S. Pat. No. 5,762,066 to Law et al. describes a high intensity ultrasound system consisting of an intracavity probe having two active ultrasound radiating surfaces with different focal geometries. U.S. Pat. No. 5,366,490 to Edwards et al. describes a method for applying destructive energy to a target tissue using a catheter. U.S. Pat. Nos. 5,207,214 and 5,613,940 to Romano describe an array of reciprocal transducers which are intended to focus intense sound energy without causing extraneous tissue damage. Finally, U.S. Pat. No. 5,241,962 to Iwama describes the use of ultrasonic pulses and echo signals to disintegrate a calculus.

Focusing of ultrasonic waves is a fundamental aspect of the most of the medical applications of ultrasound. The efficiency of ultrasound focusing in biological tissues is often significantly limited by spatial heterogeneities in sound velocity in tissues and the presence of various reflective surfaces and boundaries. The refraction, reflection and scattering of ultrasound in inhomogeneous media can greatly distort focused ultrasound field. There are many methods for improving the ultrasonic focusing in complex media based on the phase and amplitude corrections in focusing system but they are often too complicated and in some cases do not provide necessary improvement. The concept of TRA developed initially by M. Fink of the University of Paris provides an elegant possibility of both temporal and spatial concentrating of acoustic energy in highly inhomogeneous media. The TRA technique is based on the reciprocity of acoustic propagation, which implies that the time-reversed version of an incident pressure field naturally refocuses on its source. The general concept of TRA is described in an article by Fink, entitled "Time-reversed acoustics," Scientific American, November 1999, pp. 91-97, which is incorporated herein by reference. U.S. Pat. No. 5,092,336 to Fink, which is also incorporated herein by reference, describes a device for localization and focusing of acoustic waves in tissues.

An important issue in the TRA method of focusing acoustic energy is related to obtaining initial signal from the in the target area. It is necessary to have some sort of beacon to provide an initial signal from the focal region. In the TRA systems described in the prior art, most common beacon is a hydrophone placed at the chosen target point. Other possible beacons are highly reflective targets that provide an acoustical feedback signal for TRA focusing of acoustic beam. This requirement of having a beacon in the target region limits the applications of TRA focusing methods.

U.S. Pat. No. 6,161,434 to Fink et al., which is incorporated herein by reference, describes methods to use time-reversed acoustics to search for a faint sound source. U.S. Pat. No. 5,428,999 to Fink, which is also incorporated herein by reference, describes methods for detecting and locating reflecting targets, ultrasound echographic imaging, and concentrating acoustic energy on a target.

Remarkably, scattering and numerous reflections from boundaries, which may greatly limit and even completely diminish conventional focusing, lead to the improvement of the focusing ability of the TRA system. Fink et al. have demonstrated a remarkable robustness of TRA focusing: the more complex the medium, the sharper the focus.

The advantages of the TRA-based focusing systems (TRA FS) over conventional ultrasound focusing are as follows:
1. TRA FS is capable to precisely deliver ultrasound energy to the chosen region regardless of the heterogeneity of the propagation medium, for example behind the ribs or inside the skull. The ability to effectively localize ultrasound energy and avoid exposure of surrounding tissues is important in many medical applications including ultrasound surgery and the ultrasound enhanced drug delivery.
2. TRA FS can produce more effective spatial concentration of ultrasound energy than traditional systems; the focus volume can approach ultrasound diffraction limit, it can be spherical rather than elongated ellipsoidal typically formed by most traditional focusing systems.
3. TRA FS can produce pulses with arbitrary waveforms in a wide frequency band. Ability to generate various waveforms is important in many applications, for example for optimizing the outcome of the ultrasound stimulated drug delivery where the main mechanism of ultrasound action, sonoporation, is related to cavitation and the threshold of cavitation depends strongly on frequency and the form of the applied signal.

Several examples of TRA FS employing a passive ultrasound reflector or an active ultrasound emitter as a TRA beacon are described in the U.S. patent application Ser. No. 10/370,134 (US Patent Application Publication No. 2004/0162550) and U.S. patent application Ser. No. 10/370,381 (US Patent Application Publication No. 2004/0162507) to Govari et al. as well as a European Patent Application No. EP1449564, all of which are incorporated herein by reference. Described here is a TRA-based high intensity ultrasound system designed for isolation of pulmonary veins. The beacons, described in these references, are an active or passive piesotransducers designed to reflect or emit ultrasound signal to be detected by an array of transducers. In case of an active beacon, the electrical energy is typically delivered thereto via electrical leads from the control unit. The electrical energy is converted by the active beacon into the acoustic energy and transmitted to the outside the body where it is picked up by outside sensors to determine the exact location of the beacon. In some other cases, wireless circuitry and method of energy transmission is used to transmit the electrical energy to the active beacon, which is then again is converted to the acoustic energy emanated by the beacon. Alternatively, the beacon may comprise a passive ultrasound reflector, such as the one having a geometry that produces a sharp and easily distinguishable ultrasound signature. Alternative designs of the reflector include the design with substantially higher reflectivity of the ultrasound signal then that of the surrounding tissues, including the design of the beacon with predefined resonant frequency and high Q or a bubble containing an ultrasound agent.

Another important area of medical application of ultrasound is selective drug delivery, specifically for cancer treatment. Tumor chemotherapy is often associated with severe side effects caused by the interactions of cytotoxic drugs with healthy tissues. In addition, tumor cells often develop resistance to drugs in the course of chemotherapy (cross-resistance or multi-drug resistance). Direct injection of drugs in the tumor substantially reduces or eliminates side effects of chemotherapy and increases therapeutic windows of drugs.

Acoustically activated drug delivery systems are typically therapeutic agents bound to nano- or micro-scale carriers. These are administered to a patient and then activated by extracorporeal ultrasound transducers. Acoustic activation releases the therapeutic agent and induces cavitation that enhances drug uptake in the patient's cells. A high dosage of toxic drugs may be delivered to a point of interest while minimizing negative side effects.

Acoustic activation technology shows promise for the treatment of drug-resistant cancer tumors, vascular disease, and other diseases. Triggering the intracellular drug uptake by focused ultrasound enhances treatment efficacy. Ultrasound is proven to be an effective drug delivery modality. An advantage of ultrasound in this application is that it is non-invasive, can penetrate deep in the interior of the body, and can be carefully controlled via a number of parameters including frequency, power density, duty cycles, and time of application. Gene therapy researchers have reported recently a tenfold increase in DNA uptake. In-vitro experiments suggest that acoustic activation therapy may be effective in treating multidrug-resistant tumors, which are very resistant to conventional treatments. Physicians do not currently have a means to accurately sonicate only an area of interest where the drug has been injected, in order to improve drug uptake to diseased cells and reduce side effects to healthy tissue.

Non-invasive recharging of implant batteries emerges as a very important area of need for great many medical devices of today. According to the article published in Business Week on Mar. 7, 2005 on pages 74-82 by Michael Arndt and entitled "Rewiring the Body", new electrical stimulation and neurostimulation devices hold great promise to treat a variety of diseases including depression, paralysis, migraines, sleep apnea, angina, obesity, digestive tract disorders, Alzheimer's, obsessive-compulsive disorder, Parkinson's, epilepsy and many others. Already today, as many as 190,000 patients in the US are wearing electrodes in their heads to control tremors associated with Parkinson's disease and 60,000 patients have an inner ear implant to improve hearing. Advances in nerve stimulation hold tremendous promise of relief to millions of patients worldwide. There are for example up to 3 million Americans suffering with chronic migraines and about 4 million Americans who are morbidly obese. Neurostimulators hold great promise for these patients.

However, the infection risk of implantation procedure is not trivial. For cardiac pacemakers, this risk is as high as 3 to 4 percent, which is twice the infection risk of the surgery in general. Present day devices contain an internal battery, which can last as long as 5-10 years, after which time the device should be replaced with another surgery. To reduce the infection risk associated with a second implant, the need exists for a device allowing internal recharging of an existing implant battery in a non-invasive manner. Acoustic energy can be transmitted to the site of an implant. The need exists for a device allowing high-intensity energy to be directed at the exact location of an implant and then transforming that energy into electrical energy usable to recharge the implant battery. Another need exists for an internal device capable of receiving high-intensity acoustic energy and converting it to electrical power to drive various additional implant devices associated with electrical stimulators.

The need also exists in general for a system capable of more accurately focusing of acoustic energy in the region of interest inside the body. More specifically, the need exists for a method and device for TRA focusing with remote wireless feedback from the focal point without inserting a hydrophone in the target area. The need further exists for a system allowing focusing of ultrasound energy only on an area having a desired size and shape.

SUMMARY OF THE INVENTION

Accordingly, it is an object of the present invention to overcome these and other drawbacks of the prior art by providing a novel beacon, which provides TRA feedback signal in the form of an electromagnetic wave signal transmitted wirelessly as well as the system using thereof for TRA focusing of acoustic waves.

It is another object of the present invention is to provide a novel method and an electromagnetic wireless beacon adapted to focus high intensity ultrasound waves on a desired area in the patient's body.

It is a further object of the present invention to provide a method and an electromagnetic beacon with the system utilizing thereof to focus ultrasound energy on a target area having a desired size and shape.

It is yet a further object of the present invention to provide a method and a wireless beacon to generate an electromagnetic signal capable of charging internal batteries of various medical implants.

It is yet a further object of the present invention to provide an acoustical system and a wireless beacon to remotely control drug delivery from an implant.

The method and the beacon of the invention are based on using a transducer capable of generating an electromagnetic wave signal in response to being energized by acoustic waves. In its most basic form, the transducer is a piezoelectric transducer element, made for example of piezopolymer or piezoceramic material. The present invention encompasses a method of TRA focusing with remote feedback from the focal point in the form of electromagnetic waves generated by a miniature piezotransducer placed in the target area and affected by the initial acoustic wave. Once the initial acoustic wave transmission causes energizing of such piezoelectric transducer element, it generates an electromagnetic wave feedback signal reproducing exactly the waveform of the received acoustic wave, which is then emitted outside via an optionally integrated internal antenna. Such radiofrequency electromagnetic wave signal can be used by an external ultrasound system to "home-in" the acoustic waves on the beacon using Time-Reversal Acoustics principles.

Beacons of various complex shapes such as strips, tubes, spheres, etc. can be advantageously used for the purposes of the present invention to allow concentrating the ultrasound acoustic energy on a desired area having a complex shape and size, as defined by the size and shape of the piezoelectric element itself.

The invention obviates the need to have a wired connection to the beacon used for ultrasound guidance in the prior art and makes the instrument utilizing the system of the invention easier to use.

The present invention further encompasses a method and device for remotely charging the batteries of the devices implanted in the soft biological tissue. According to the present invention, TRA focusing may be used to deliver acoustic energy precisely to the piezoelectric element of the invention incorporated into or attached to the implanted device and used for such charging. Upon conversion of the acoustic energy into electric energy, such device is advantageously used to remotely and non-invasively recharge an internal battery of an implant such as a pacemaker, neurostimulator, and alike. Examples of implants are discussed in greater detail above as well in the above-referenced article from Business Week magazine. Importantly for this invention, such device can be used for both charging the battery and also acting as a beacon for the TRA focusing.

The invention can also be used advantageously for remotely controlled drug eluting from the implants comprising a piezomaterial (e.g. piezopolymer fibers).

The invention further encompasses an integrated device for image-guided drug delivery for enhanced efficacy of cancer treatment.

The invention further encompasses a novel TRA transmitter formed by an acoustical reverberation chamber, which comprises piezotransducers mounted in the inner cavity of said chamber so that their electrical field is fully shielded and only acoustic wave escapes from the TRA transmitter. This greatly increases the signal-to-noise ratio for the feedback radio (electromagnetic) signal from the beacon of the invention that is used for tuning the TRA focusing system.

Since one of the objects of the invention is to focus and concentrate acoustic energy within the biological soft tissue, the invention also encompasses means for increasing the output of the TRA focusing transmitter by improving the acoustical matching of the transmitter with biological tissue. This is achieved by a design of the TRA resonator such that the acoustic energy, which is bouncing and accumulating in the resonator, is transformed into the flexural (bending) type acoustic wave using a facet spaced apart from the main body of the transmitter. Such wave has greater amplitude and is better matched with biological tissues.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
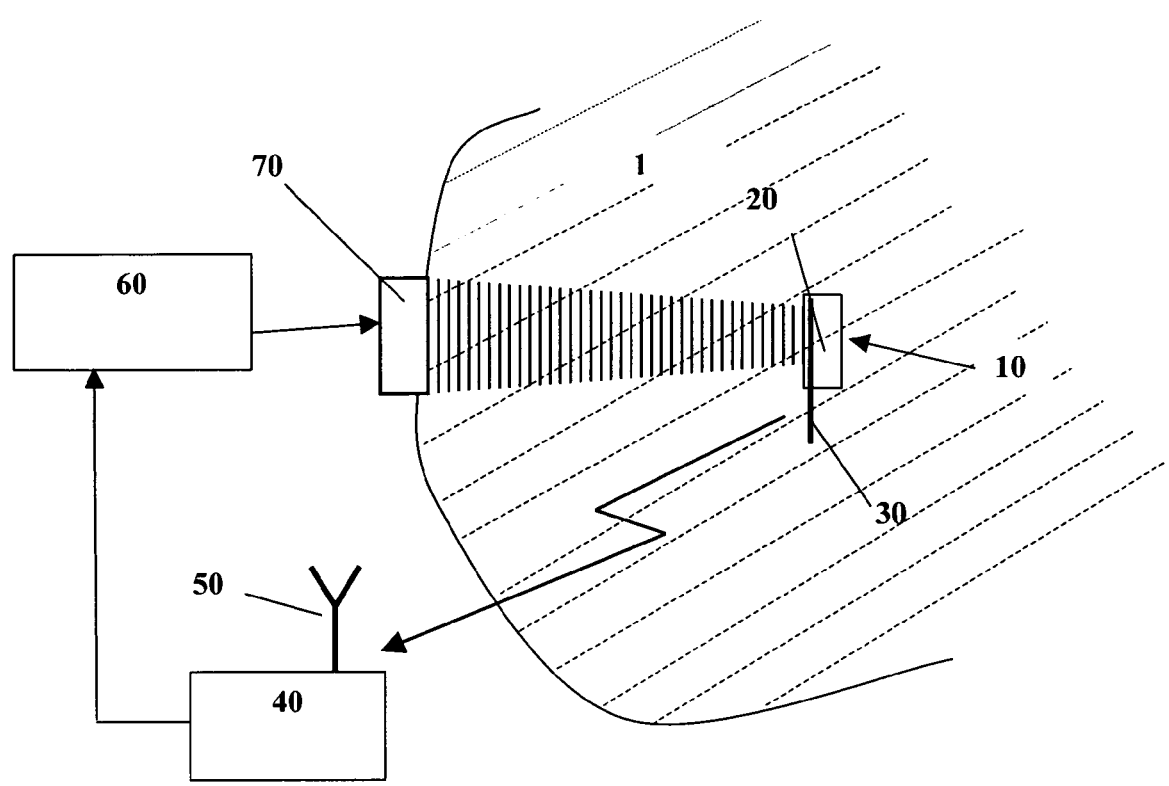
FIG. 1 is a general schematic depiction of the wireless beacon and the system of the invention.

FIG. 1 shows a schematic diagram of the beacon and system of the invention. It shows the beacon 10 located inside a patient's body 1 at a desired location for focusing ultrasound energy. It may be connected to or be an integral part of an optional medical instrument (not shown in the drawing). It consists of two main components: piezoelectric element such as a transducer 20 and an optional emitting antenna 30. Some examples of the details of the design of the beacon 10 are described below.

The TRA part of the system comprises a TRA electronic unit 60 connected to the transmitter 70. The TRA electronic unit 60 provides recording and storing in the memory of the electromagnetic wave signal received from the beacon 10, reversing it in time, amplifying and sending it as a driving signal to the transmitter 70. The transmitter 70 is typically placed over the skin of the patient as shown on the drawing. Feedback to the TRA electronic unit 60 is provided by the radiofrequency receiver 40 equipped with the receiving antenna 50. Antenna 50 is adapted to receive electromagnetic wave signals generated by the piezoelectric transducer element 20 of the beacon 10 in response to the acoustic pulse radiated by the TRA transmitter 70.

Figure 2:
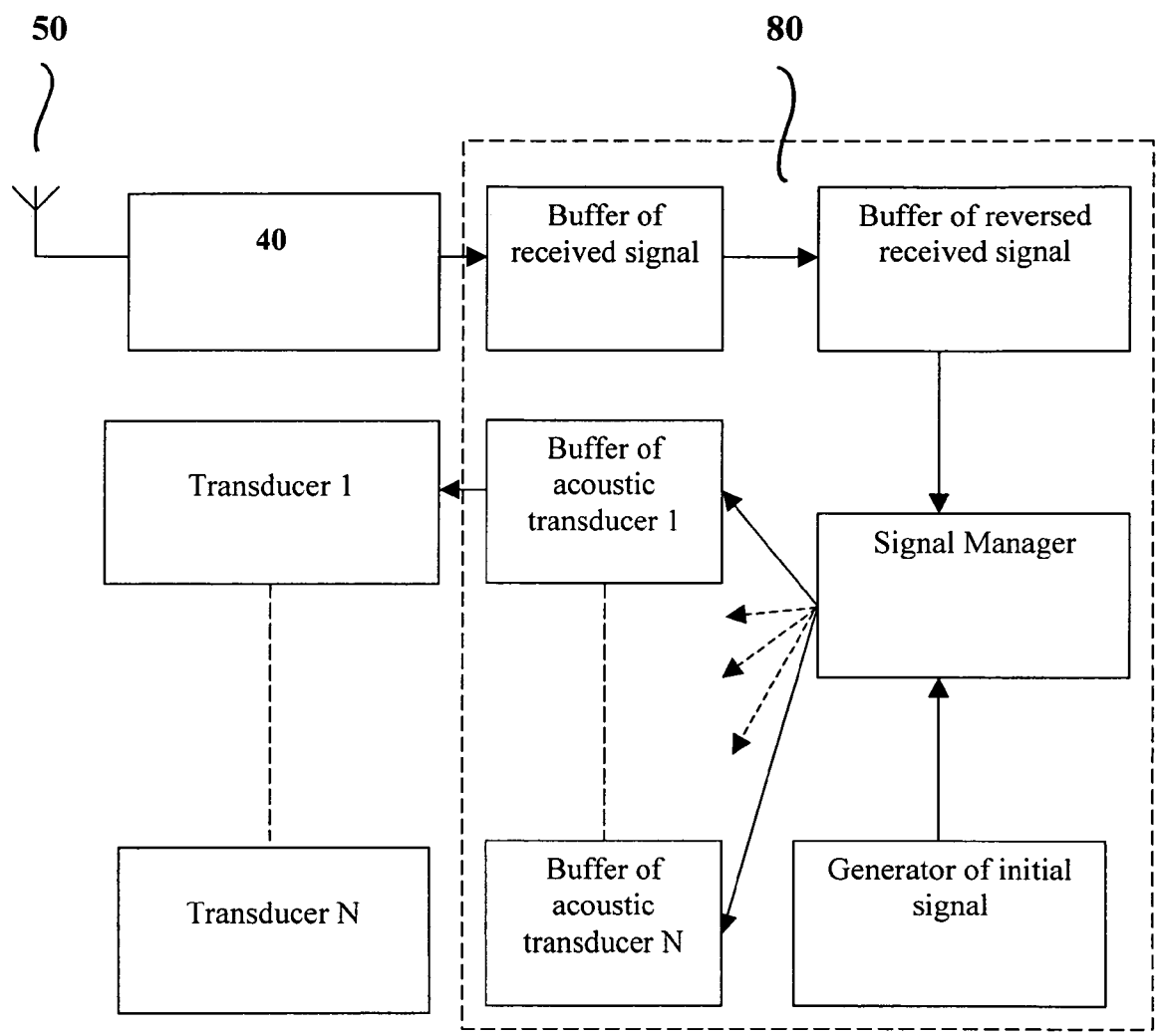
FIG. 2 shows a block-diagram of the multi-channel TRA electronic unit of the present invention.
Figure 3:
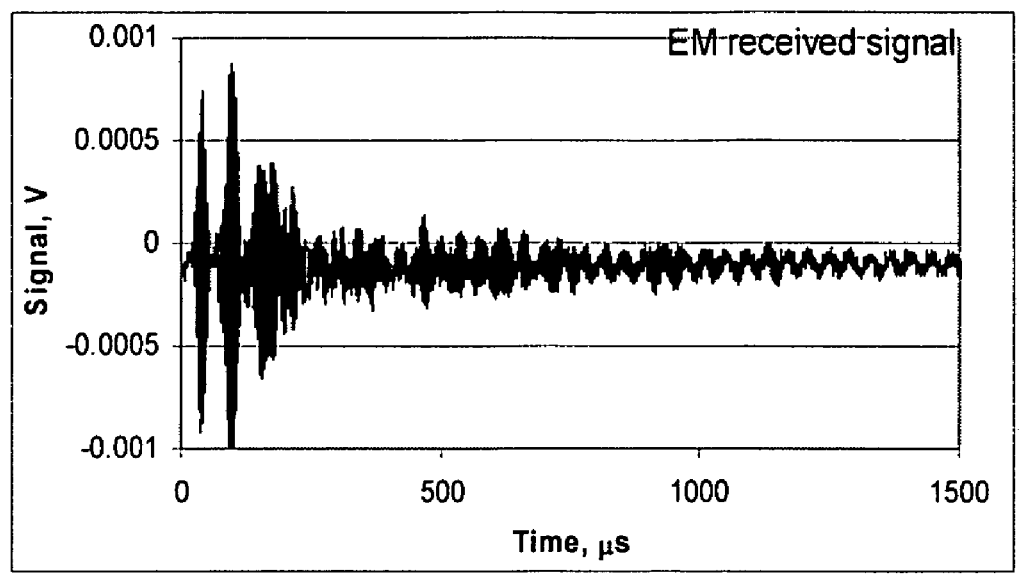
FIG. 3 shows an example of the electromagnetic wave signal received remotely from the beacon-piezotransducer of the present invention used according to the diagram in FIG. 1.

FIG. 2 presents a block-diagram of a multi channel TRA system. In use, the buffer of the initial signal contains a sample waveform, which is first sent individually to each of the acoustic transmitters one at a time. Each transmitter then sends the initial acoustic signal through the tissue such that the piezoelectric element 20 of the beacon 10 receives it individually and also one at a time. The initial acoustic signal is then transformed into an electromagnetic wave feedback signal and sent back by the antenna 30 of the beacon 10. The radio receiver 40 receives that electromagnetic wave feedback signal by its antenna 50 and sends the signal to the buffer of received signals. FIG. 3 shows an example of a signal received remotely from the piezotransducer 20 of the present invention by the TRA electronic unit 60 in response to an initial signal from the TRA transmitter 70. Once received, this signal is time reversed by the signal processor as described above. It is then sent as an individual driving signal to the respective buffer of each acoustic transducer. Once the operation of focusing acoustic signals is concluded for all transducers, the TRA generated driving signals are sent to all transducers at the same time, meaning they are synchronized with the initial signal. As a result, a high level of superimposed acoustic energy is closely focused on the area of the piezoelectric element and sent only to the location of the wireless beacon and not to the surrounding tissues.

The block-diagram of the TRA electronic unit comprising the radio wave (electromagnetic wave) receiver 40, the signal processor 80 and either one or many transmitting transducers is shown in greater detail in FIG. 2. The operation of the system includes the following method steps in accordance with the general principles of operation described above:

Step 1. Applying a short initial pulsed signal to the first transducer. The initial pulse is provided by a signal generator containing in its memory a library of the pulses used for the initial signal.

Step 2. Receiving a electromagnetic wave feedback signal by receiver 40, time reversing it and storing in the memory of the buffer of the first acoustic transducer. An example of the received radio signal is shown in FIG. 3.

Step 3. Repeating steps 1 and 2 for each transducer, if present.

Figure 4:
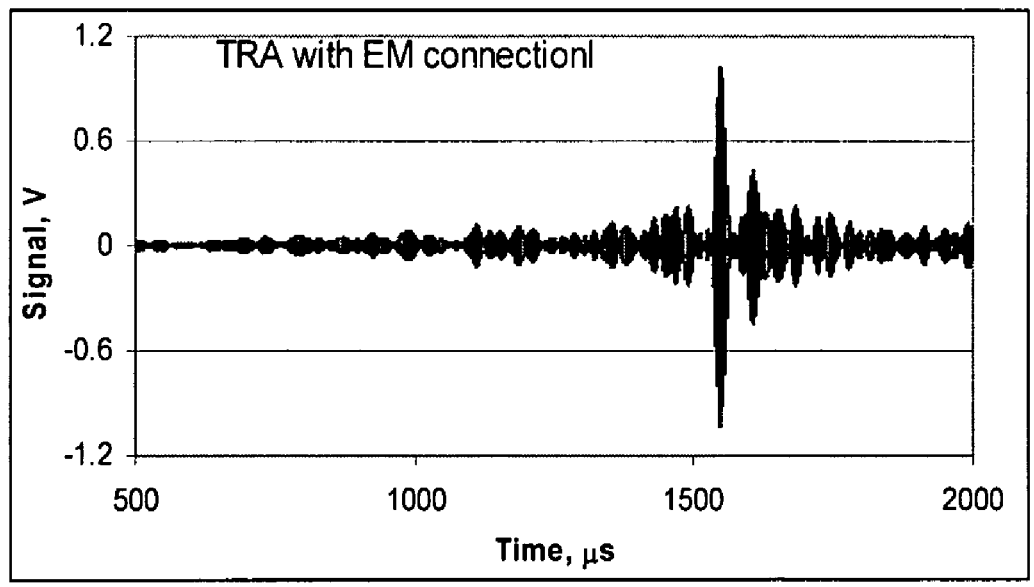
FIG. 4 is an example of TRA focused signal generated using electromagnetic wave feedback signal from the beacon-transducer of the present invention used according to the diagram in FIG. 1.

Step 4. Radiating simultaneously the time reversed signals stored in the buffer of all transmitting transducers as synchronized with the initial signal. This simultaneous radiation results in focusing of acoustic waves generated by all transmitting transducers at the location of the beacon 10. As a result of such focusing, a greatly enhanced electromagnetic wave signal is detected by the receiver 40. An example of such signal is shown in FIG. 4.

Step 5. Repeating Step 4 as many times as necessary for achieving the required effect.

In certain preferred applications of the present invention such as remote charging of batteries of the implanted devices, Steps 1 to 3 need to be repeated to adjust the focusing of the system since the beacon 10 may be shifted from its initial position. The criterion for repeating the focusing steps is a decrease of the amplitude of the electromagnetic wave signal detected by the receiver 40 and stored in the buffer in comparison with the previous signal level.

Importantly, the electromagnetic wave feedback signal is generated by the piezoelectric element to represent cumulatively all the acoustic waves as received by that piezoelectric element. As a result of this integrated generation of the electromagnetic wave feedback signal, its content reflects the size and shape of the piezoelectric element itself. This feature of the device can be advantageously used in delivering high intensity acoustic waves to the desired region in the desired shape, as this shape is defined by the shape of the piezoelectric element. Highly sophisticated shapes can be selected based on the needs of particular applications. For selective tissue fusing for example, a circular ring shape of the piezoelectric element may be chosen to deliver high intensity acoustic energy to a periphery of a circular target.

Figure 5:
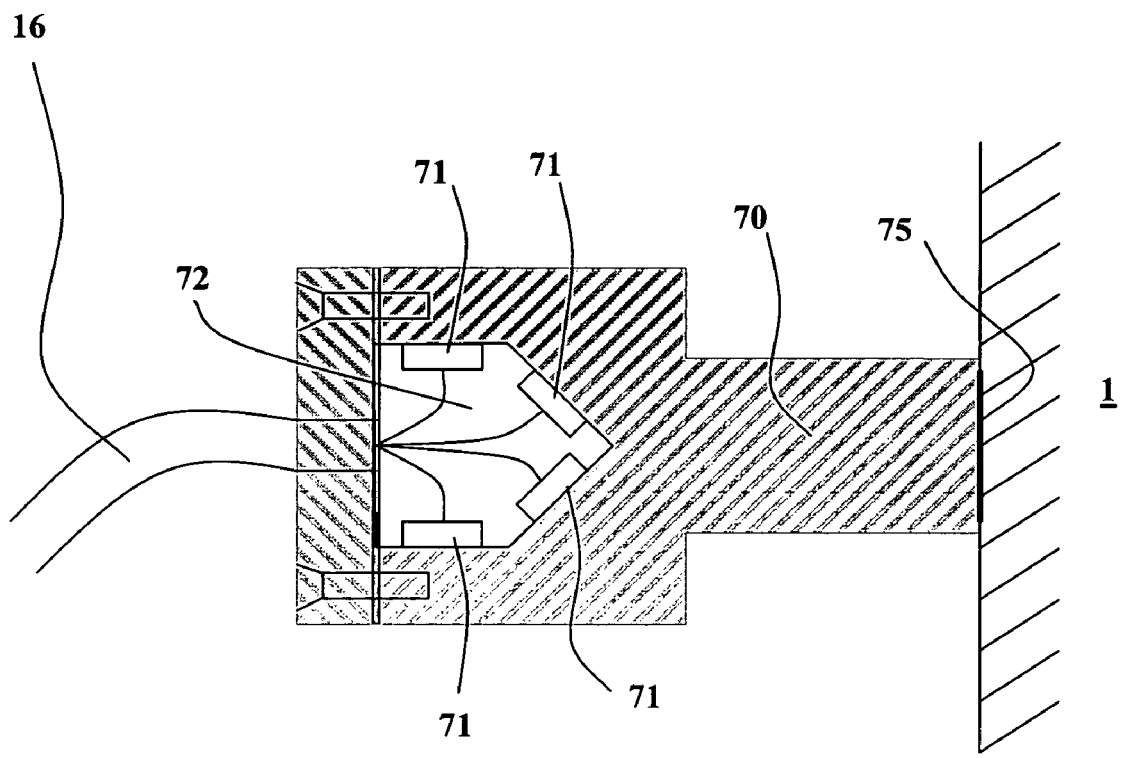
FIG. 5 shows a cross-sectional view of the TRA focusing transmitter with piezotransducers placed in its inner cavity.
Figure 6:
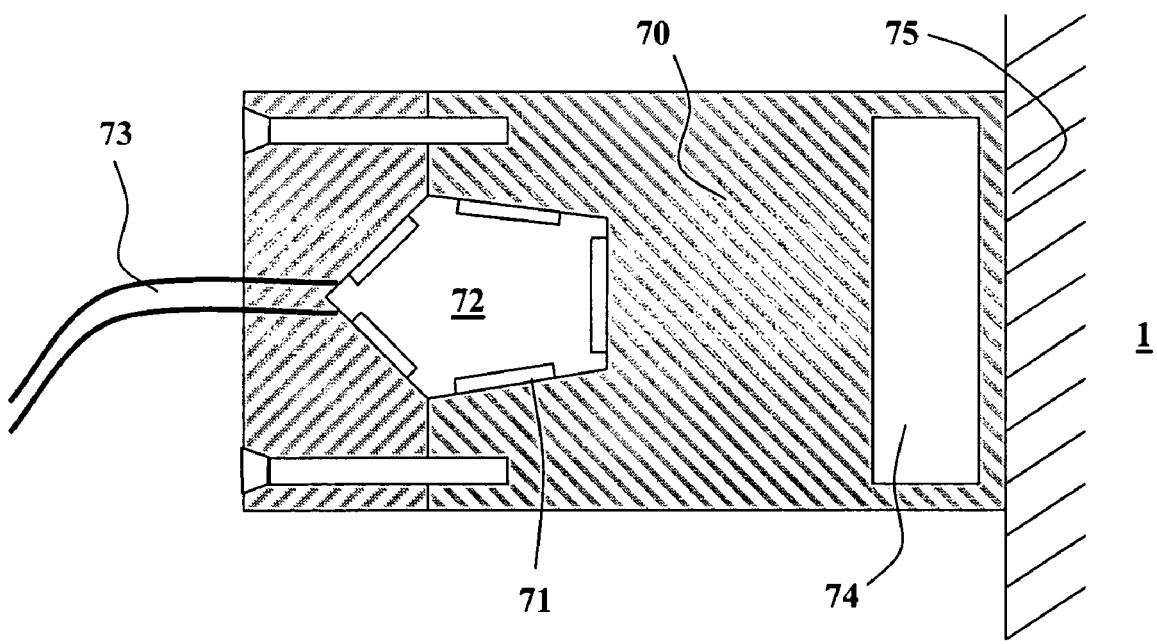
FIG. 6 shows a cross-sectional view of the TRA focusing transmitter with the acoustical mode conversion and a spaced apart facet.

Since TRA focusing of ultrasonic waves in the present invention uses radio electromagnetic waves as a feedback signal for tuning the system, it is important to eliminate radiation of electromagnetic waves from any source other than the beacon 10. FIGS. 5 and 6 show embodiments of the TRA focusing transmitter 70 meeting this requirement of minimizing the radiation of electromagnetic waves during their operation. To achieve that goal and shield the transducers and connecting wires of the cable 73, the transducers 71 are mounted inside the internal cavity 72 formed inside the transmitter. The transmitter is preferably made of material with low attenuation of ultrasound, such as aluminum, to provide long reverberation time of acoustic signal in the body of the transmitter. Longer reverberation is important for the TRA mode of operation because it helps to accumulate more acoustic energy in time. The alternate transmitter design shown in FIG. 6 has an additional feature: improved coupling with the patient's tissue 1 using a cavity 74. Since the tissue is much more compliant than solid material of the transmitter, only a small fraction of the generated acoustic energy is radiated into the tissue 1. There is a possibility to decrease the compliance of the transmitter using a different acoustical mode of oscillation of the transmitter facet contacting the tissue 1. In the embodiment shown in FIG. 6, the longitudinal (compressional) acoustic waves generated by the piezotransducers, are converted into more compliant flexural mode of oscillation at the radiating surface 75 of the transmitter 70.

Figure 7:
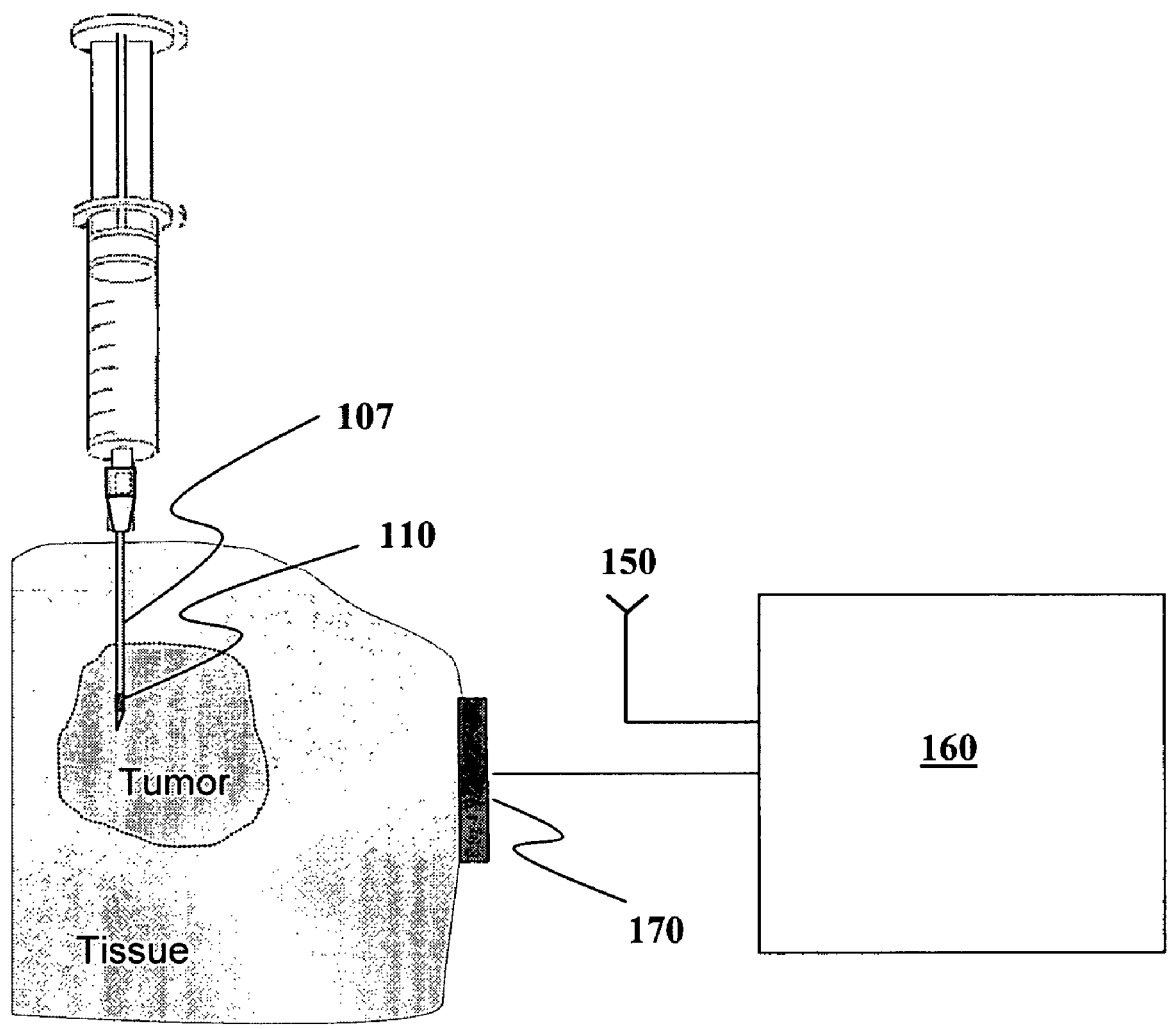
FIG. 7 is a general schematic depiction of the system of the invention when used for local drug delivery.

Use of the Invention as an Acoustically Enhanced Image-Guided Drug Delivery Apparatus FIG. 7 depicts one advantageous use of the present invention—acoustically activated system for target tissue imaging, needle path tracking and ultrasound assisted drug delivery based on TRA focusing of ultrasound energy on the target tissue. This system may be especially useful in treating cancer tumors.

Generally, chemotherapy targets the cancerous cells by attacking cells that undergo frequent cell division. Active cell growth is the most common criteria used to differentiate tumor cells from normal cells. Because some normal cells in the body undergo physiological cell growth, such as blood cells and cells in the bone marrow, many cancer drugs must be limited in dose to prevent lethal toxicity arising from damage to these healthy cells. Therefore, needle injection of the chemotherapeutic agent directly to the tumor site remains a viable solution. Image guidance of needle-based delivery and energy-enhancement of the drug uptake by cancer cells are desired to achieve best possible outcome.

According to the invention, an ultrasound imaging is first used to visualize a tumor and guide direct needle-based delivery of encapsulated, drug-contained nanoparticles to the selected site. A "smart needle" with a piezoelectric strip mounted at its tip will be used to provide unmistakable trace of the needle path. Then, the same integrated acoustic system will trigger and enhance intracellular uptake of the injected drug by high intensity ultrasonic field created using the Time Reversal Acoustic (TRA) technique. Piezoelectric strip mounted at the tip of "smart needle" will act as a beacon for the TRA focusing of ultrasound in the selected site of the tissue to preferentially release the drug. Accurate tailoring of the geometry of the high intensity ultrasonic field to preferentially treat the target site of tissue can be achieved with the TRA technique much more efficiently than by conventional ultrasonic methods.

FIG. 7 depicts the integrated ultrasonic system for image guided drug delivery such as needed for example for cancer treatment. The needle 107 is equipped with a piezofilm 110 serving as a piezoelectric transducer element generating an electromagnetic wave signal to be transmitted by an emitting antenna incorporated along the needle 107 (antenna not shown on the drawing). The TRA transmitter 170 is activated by the combined ultrasonic imaging and TRA treatment electronic unit 160. It is in turn designed for providing both a tumor image (for needle and drug delivery guidance) and therapeutically acceptable ultrasound energy signal through the TRA transducer array 170.

In the preferred method of use, a physician inserts the smart needle 107 to a depth within a patient. The insertion is made under the guidance by an ultrasonic scanner. Ultrasonic image shows anatomical structures represented by spatial distribution of ultrasound scatterers in the tissue. The tip of the needle, as the only "active" scatterer, provides much brighter trace than any portion of the imaged tissue that passively scatters ultrasound. Consequently, the insertion process and the needle tip trajectory are clearly visualized. Reliable image guided needle insertion and localized drug delivery method to a depth within a patient may increase the potential number of tumor types to be treated. Once the needle is positioned at the chosen site within the tumor, the drug is injected. Simultaneously, the smart needle provides a feedback signal for tuning the TRA FS, which enables accurate focusing of ultrasound energy in the tumor. After the needle is removed from the tissue, the TRA system generates highly localized ultrasonic field within the tumor with required spatial, temporal and energy parameters for enhancing the therapeutic efficacy of the encapsulated drug.

In its most basic form, the smart needle can be modeled by a piezopolymer film wrapped around the distal tip of a regular needle of the appropriate size.

The piezopolymer film may be preferably made from polyvinylidene fluoride (PVDF). This material is commercially available and its properties, including resistance or conditional resistance to a wide range of chemicals, are well understood. The smart needle should undergo surface treatment or thin film deposition to enhance its biocompatibility, corrosion resistance, chemical compatibility, microbial resistance, etc.

Figure 8:
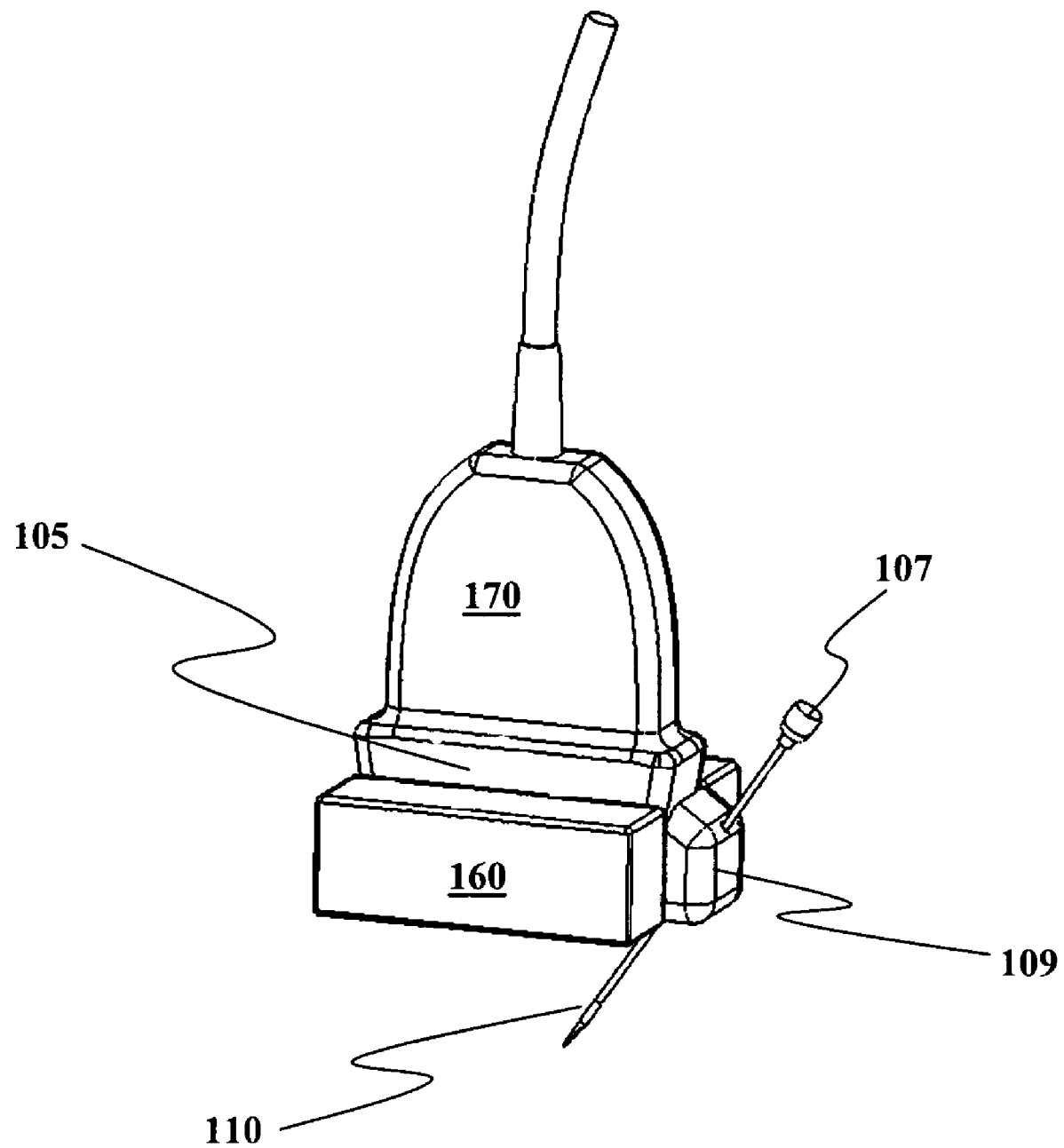
FIG. 8 is the general view of a combined ultrasound probe with TRA resonators attached along the sides of imaging array shown here with an optional needle guide.
Figure 9:
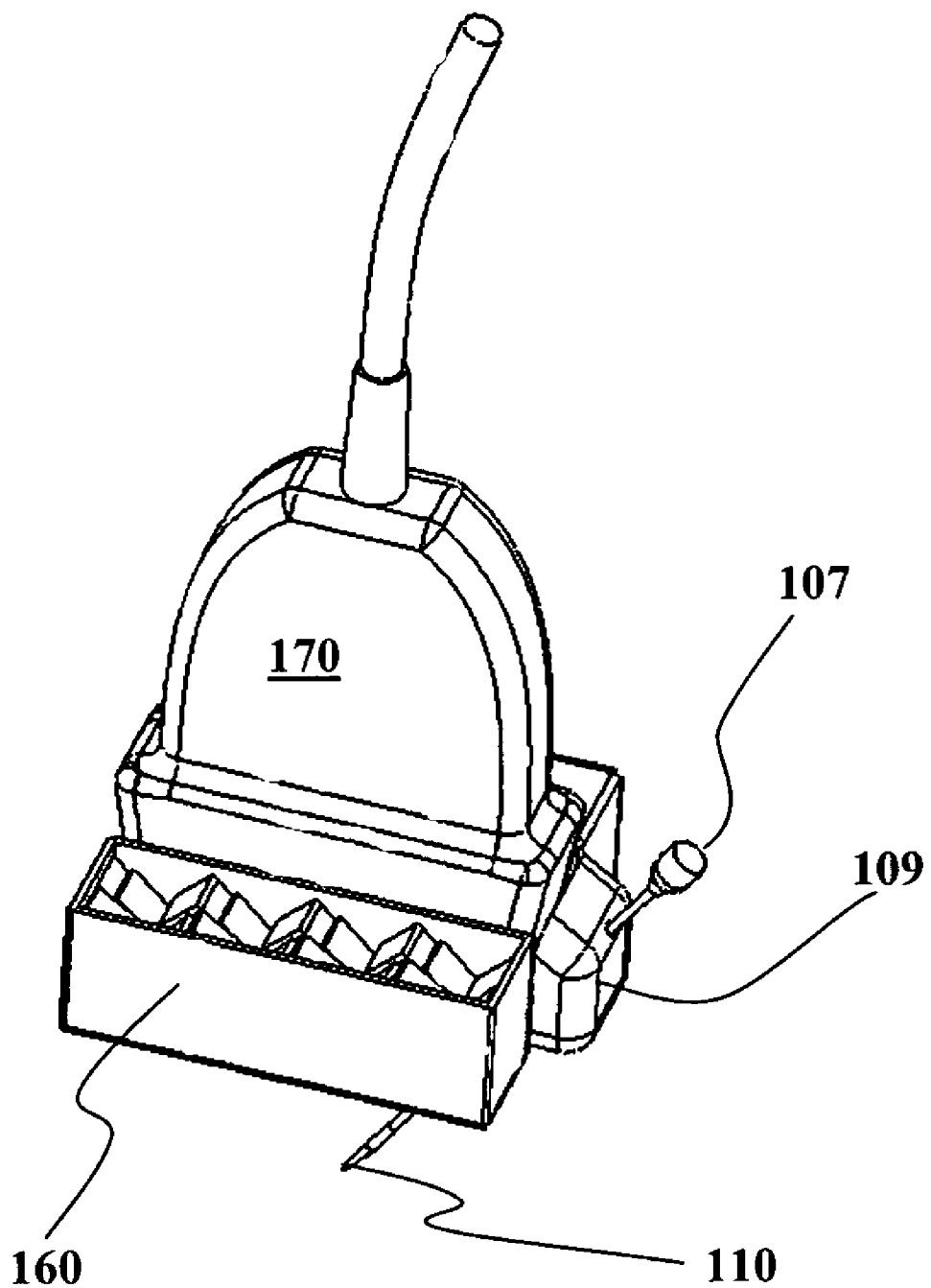
FIG. 9 is the top view of the device shown on FIG. 8 showing the details of TRA resonators.
Figure 10:
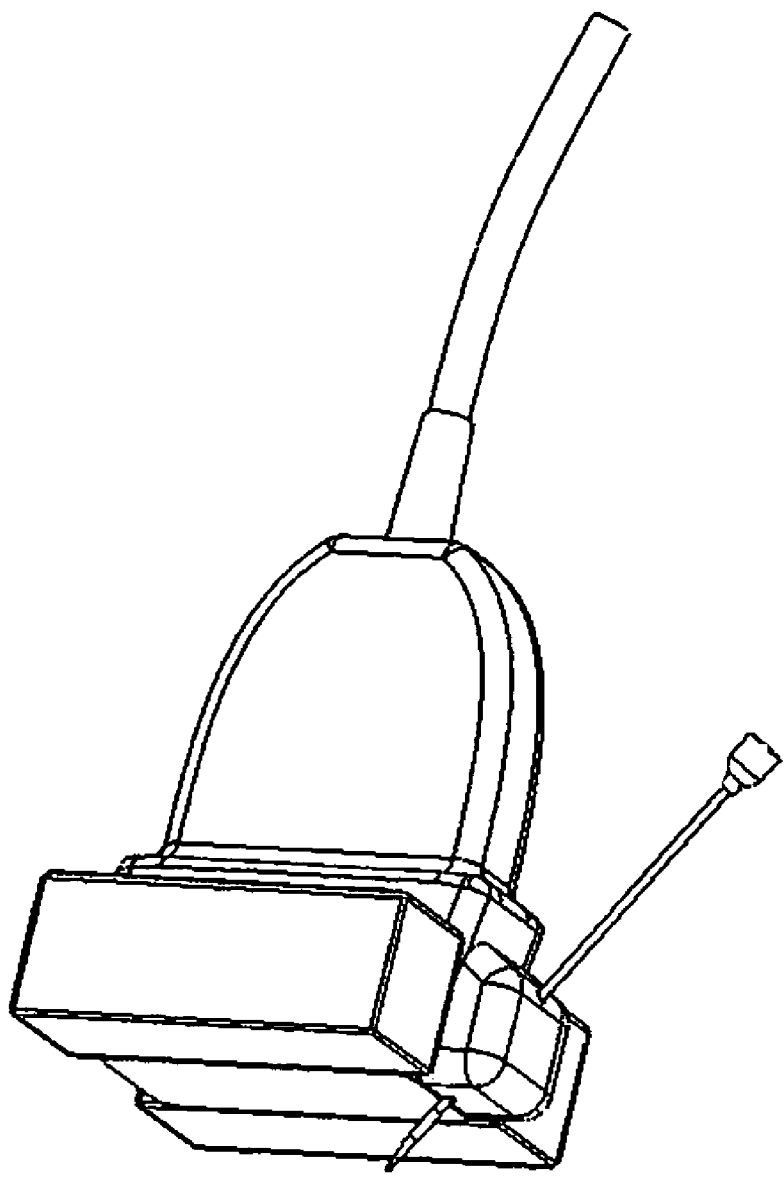
FIG. 10 is the bottom view of the device shown on FIG. 8.

FIGS. 8, 9, and 10 show the details of the ultrasound image-guided apparatus used with the smart needle of the invention. Shown on these drawings is a generic ultrasound probe combined with TRA resonators attached along the sides of the imaging array of the probe. An optional needle guide may also be used with this device. An integrated acoustic system shown on the drawings is capable of simultaneous ultrasound image-guided needle insertion and the TRA-based ultrasound assisted drug delivery.

The high frequency imaging probe 170 is combined with TRA resonator 160 containing an integrated antenna (not shown) for wireless connection with needle 107. Since the probe 110 will always be the in the vicinity of the tip of the needle 107, incorporating the emitting antenna (not shown) with the probe 110 is an appropriate solution. FIGS. 8-10 show the imaging probe 170 positioned in the middle and surrounded by two low frequency TRA resonators 160. An optional needle guide 109 is used for positioning the needle 107 during insertion. Each one of two acoustic resonators 160, attached to the long sides of the ultrasound imaging array 105, comprises numerous TRA transducers as described above. These transducers are individually connected with the output channels of the TRA focusing system.

Of course, as a useful subset of the system described above, an image-guided portion of the device can be advantageously used by itself for various medical applications without acoustically enhanced drug delivery portion.

Use of the Invention for Remote Charging of Implant Batteries

The present invention can be used for remotely charging the batteries of the devices implanted in the soft biological tissue or another inaccessible object. Remote recharging of batteries of internal implants, such as urinary tract control devices, cardiac pacemakers, cochlea implants and deep brain neurostimulators among others is an important problem to which there is no adequate solution. As described in greater detail above in the background section of this specification, recharging of an implant battery in a noninvasive manner would allow avoiding a second operation of replacing the originally placed device. Additional advantageous use is to drive on demand an otherwise passive electrically activated device.

Although it was known before that the energy of the focused ultrasound can be transformed to electric current for battery recharge, the difficulty of doing so is that conventional focusing means cannot very accurately concentrate high levels of acoustic energy on the implanted device without affecting surrounding tissues. According to the present invention, TRA focusing may be used to deliver acoustic energy precisely to the piezoelement of the invention used for charging the battery and also acting as a beacon for the TRA focusing.

Figure 11:
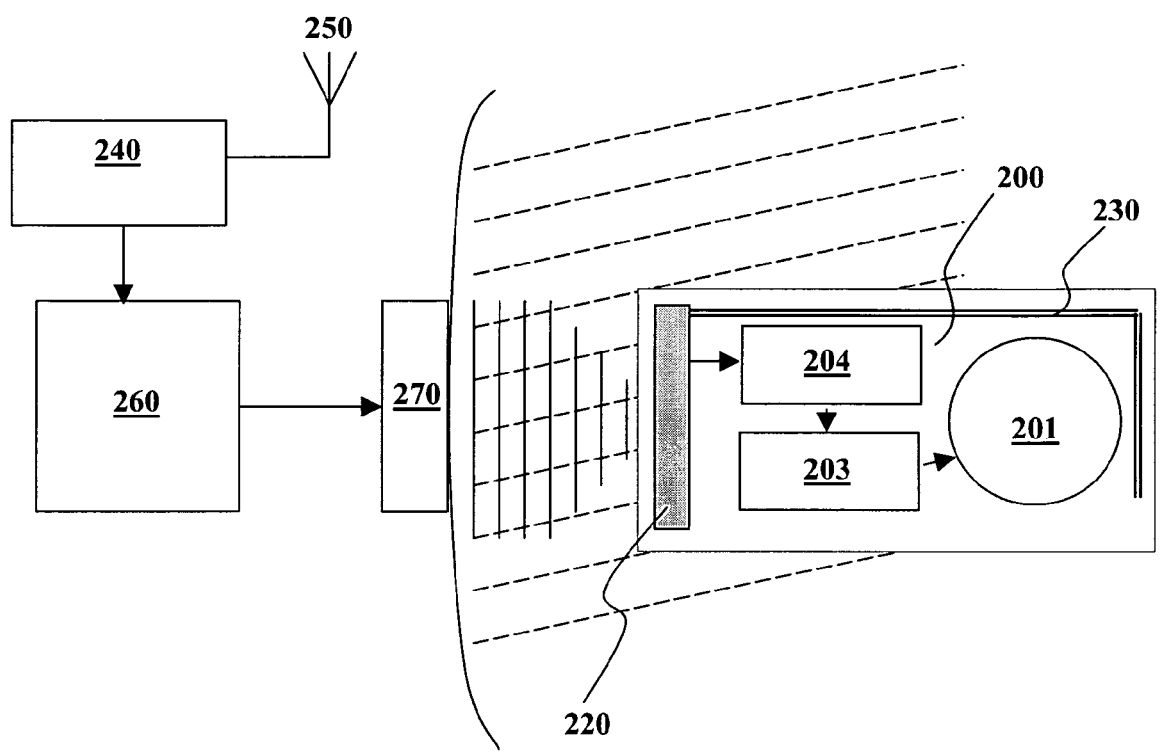
FIG. 11 is a general schematic illustration of the system of the invention when used for charging the implant batteries.

FIG. 11 shows a general schematic depiction of this use of the invention. The TRA electronic unit is similar to the one depicted on FIG. 2 and described above in greater detail. The implant 200 is equipped with a piezoelectric transducer element 220 and the emitting antenna 230. Charging of the battery 201 is achieved by a transformer 204 of the mechanical acoustic signal into an electric signal to activate the battery charger 203.

The TRA system consists of a radio receiver 240 equipped with a receiving antenna 250 and connected to the TRA electronic unit 260. The TRA unit 260 in turn is adapted to transmit TRA-based signals through the TRA transducer 270 and concentrate acoustic energy only on the piezoelectric element 220. Electrical power generated via the piezoelement 220 is used to charge the batteries of the implant 200.

Use of the Invention for Remotely Controlled Drug Eluting from Implants

Another advantageous use of the invention is to activate acoustically controlled release of drugs from the implant, such as a vessel stent coated with encapsulated medication appropriate for release after the implant is imbedded in the patient's body. A piezoelectric beacon is incorporated with the implant and is designed similarly to that described above. The purpose of such beacon is to serve as a tag to enable precise focusing acoustic energy on the implant. The TRA FS system designed based on the principles described on FIG. 1 and in the above description, would be used to deliver high levels of ultrasound energy to the site of the implant thus enhancing the diffusion of the drug and releasing thereof into the area surrounding the implant.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A time-reversal acoustics system comprising:
   a wireless beacon including a piezoelectric element, and
   a time-reversal electronic unit having an input connected to an electromagnetic wave receiver and an output connected to an acoustic transmitter means,
   wherein said electronic unit is to provide said acoustic transmitter means with an initial signal a driving signal formed by time-reversing of an electromagnetic wave feedback signal received from said wireless beacon via the electromagnetic wave receiver in response to an acoustic wave signal generated by said acoustic transmitter means.

2. The time-reversal acoustics system as in claim 1, wherein said wireless beacon further including an emitting antenna connected to said piezoelectric element and adapted to transmit said electromagnetic wave signal.

3. The time-reversal acoustics system as in claim 1, wherein said electromagnetic wave receiver is further equipped with a receiving antenna adapted to receive said electromagnetic wave signal from said wireless beacon.

4. The time-reversal acoustics system as in claim 1, wherein said acoustic transmitter means comprising a plurality of transducers, said electronic unit adapted to send said initial signal to each transducer individually, said electronic unit adapted to send simultaneously driving signals synchronized with said initial signal to all respective transducers.

5. The time-reversal acoustics system as in claim 1, wherein said acoustic transmitter means including a transmitter having an internal cavity, said acoustic transmitter means further including at least one acoustic transducer mounted in said internal cavity of said transmitter.

6. The time-reversal acoustics system as in claim 5 including a plurality of acoustic transducers mounted in said internal cavity.

7. A method for delivery of focused acoustic energy to a target area in an object, said method comprising the steps of:
   a) providing a time-reversal system comprising a time-reversal electronic unit having an input connected to an electromagnetic wave receiver and an output connected to an acoustic transmitter means positioned in contact with said object,
   b) providing a wireless beacon positioned at the target area and including a piezoelectric element,
   c) generating an initial signal by said electronic unit to cause said acoustic transmitter means to send an initial acoustic wave towards said wireless beacon,
   d) generating an initial electromagnetic wave signal by said wireless beacon in response to said initial acoustic wave,
   e) receiving said initial electromagnetic wave signal by said electromagnetic wave receiver and sending it to the input of said electronic unit,
   f) generating a driving signal formed by time-reversing of said initial electromagnetic wave signal, and
   g) sending said driving signal to said acoustic transmitter means to generate an acoustic wave to deliver focused acoustic energy to said target area in said object.

8. The method as in claim 7, wherein said acoustic transmitter means including a plurality of transducers, said steps (c) through (f) are repeated one at a time for each individual transducer to generate individual driving signals, said step (g) including sending all said individual driving signals simultaneously to all respective transducers, said individual driving signals being synchronized with respect to the corresponding initial signal.

9. The method as in claim 8, wherein said step (g) including repeatedly sending said driving signals to said transducers.

10. The method as in claim 7 or claim 8, wherein said steps (c) through (f) are repeated once the amplitude of said electromagnetic wave signal drops below a predetermined level.

* * * * *